US00PP18233P2

(12) United States Plant Patent
Gossett

(10) Patent No.: US PP18,233 P2
(45) Date of Patent: Nov. 20, 2007

(54) ***PENSTEMON* PLANT NAMED 'CRUSHED GRAPES'**

(50) Latin Name: ***Penstemon* spp.**
Varietal Denomination: Crushed Grapes

(75) Inventor: Gary J. Gossett, Portland, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 26 days.

(21) Appl. No.: 11/452,686

(22) Filed: Jun. 13, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Annette H Para
(74) *Attorney, Agent, or Firm*—Klarquist Sparkman, LLP

(57) ABSTRACT

A new and distinct *Penstemon* plant characterized by purple flowers on numerous, very short, flowering stems, and with a compact habit.

1 Drawing Sheet

Botanical classification: *Penstemon* spp.
Variety denomination: 'Crushed Grapes'.

BACKGROUND OF THE INVENTION

The present invention relates to a new and distinct cultivar of a suffrutescent perennial, *Penstemon* hybrid, and is given the cultivar name, 'Crushed Grapes'. *Penstemon* are in the family Scrophulariaceae. This new cultivar which originated as an open pollinated seedling from *Penstemon* 'Sweet Grapes' (U.S. Plant Pat. No. 13,549) progeny. Selections had been made yearly to improve the habit by making it more compact as well as to increase the bloom number, the number of inflorescences, and to reduce the height of the flower stalks.

SUMMARY OF THE INVENTION

This new cultivar is characterized by:

1) Deep purple flowers.
2) High flower number on a tight inflorescence.
3) Persistent basal foliage with a compact habit.
4) Numerous short flowering stalks.

This new cultivar has been reproduced only by asexual propagation (cuttings). Each of the progeny exhibits identical characteristics to the original plant. Asexual propagation by tip cuttings using standard propagation techniques with terminal and lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The drawing shows a two-year-old *Penstemon* 'Crushed Grapes' growing in the ground in full sun in the trial garden in Canby, Oreg.

DETAILED PLANT DESCRIPTION

The following is a detailed description of the new *Penstemon* hybrid based on observations of two-year-old specimens grown in the ground in full sun under typical outdoor conditions in Canby, Oreg. Canby is in Zone 8 on the USDA Hardiness map. Temperatures range from a high of 95 degrees F. in August to 32 degrees F. in January. Normal rainfall in Canby is 42.8 inches per year in the trial fields in Canby, Oreg. The color descriptions are all based on The Royal Horticultural Society Colour Chart.

Plant:
- *Type.*—Herbaceous perennial.
- *Form.*—Compact basal rosette.
- *Hardiness.*—USDA Zone 4 to 9.
- *Size.*—15 cm tall and 35 cm wide, not including bloom.
- *Habit.*—Suffrutescent, foliage doesn't die down in the winter.
- *Vigor.*—Good.
- *Roots.*—Fibrous, freely branching, white in color, White 155A. Roots develop slowly from stem cuttings.

Stem leaves:
- *Type.*—Simple.
- *Arrangement.*—Opposite on internodes growing to 4 cm.
- *Shape.*—Lanceolate.
- *Venation.*—Pinnate.
- *Margins.*—Entire, somewhat undulate.
- *Apex.*—Acuminate, tips often curl to one side.
- *Base.*—Sessile.
- *Blade size.*—Grows to 9 to 13 cm long and 14 to 18 mm wide.
- *Surface texture.*—Glabrous, shiny.
- *Leaf color.*—Deep green, between Yellow Green 147A and Green 137A top and bottom, with prominent main vein on bottom, Yellow Green 145B.

Basal leaves: Same as above except internodes only grow to 0.5 cm and leaves only grow to 5 cm long and 1.5 cm wide, petiolate, petioles 3 mm long and 1 mm wide, Yellow Green 145B.

Inflorescence:

*Type.*—Thyrse, virgate and weakly secund.

*Number of flowers.*—30 to 40 per thyrse.

*Peduncle.*—Grows to 20 cm tall and 6 mm wide, between Yellow Green 145B, glabrous (see Stem leaves above for leaves).

*Pedicel.*—Grows to 1 cm long, glabrous, Yellow Green 145B.

*Bloom period.*—June to July.

Flower bud:

*Size.*—3 cm long and 8 mm wide.

*Description.*—Closed tubular, bulging.

*Color.*—Purple 77A.

Flower:

*Type.*—Perfect, zygomorphic.

*Shape.*—Tubular, bilabiate, with a narrow tube for 5 mm, inflating for 16 mm, flaring into the lobes, the two top lobes shallowly cut and three bottom more deeply divided, flare down, and curl back at the sides.

*Size.*—3.5 cm long and 17 mm wide at flare.

*Color.*—Purple 77A on upper lobes and tube with White 155D in a band at the base of the lower lobes and Purple 77B on lower lobes, back side is Purple 77B.

*Calyx.*—5 lobes, cut ⅔ to base, overlapping, ovate shaped lobes, margins irregularly serrate, acuminate tip, campanulate, 5 mm deep and 3.5 mm wide, Yellow Green 145A.

*Stamen.*—5, one sterile without an anther, held within the corolla, filaments 20 mm long, White 155A, bearded Purple 70A on top side and Purple 75A on bottom side, anthers 2.5 mm long, pollen Yellow White 158B.

*Pistil.*—2 cm long, ovary 3 mm long and Yellow Green 146C, style 15 mm, Yellow White 158D.

*Fragrance.*—None.

*Lastingness.*—Each thyrse blooms for about 3 weeks on the plant.

Fruit:

*Type.*—Capsule.

*Fertility.*—Good.

*Size.*—1.2 cm deep and 4 mm wide.

*Color.*—Brown 200A to B.

Seed:

*Shape.*—Irregular.

*Size.*—2 mm long.

*Color.*—Brown 200A.

Disease and pest resistance: Excellent disease tolerance to root rot, a common problem for *Penstemon.* Leaf spot, rust, and powdery mildew may be a problem, but have not been observed on *Penstemon* 'Crushed Grapes'.

Comparisons to Similar *Penstemon*

Compared to *Penstemon* 'Sweet Grapes' (U.S. Plant Pat. No. 13,549), this new cultivar has shorter and more numerous flowering stems.

I claim:

1. A new and distinct *Penstemon* plant substantially as shown and described.

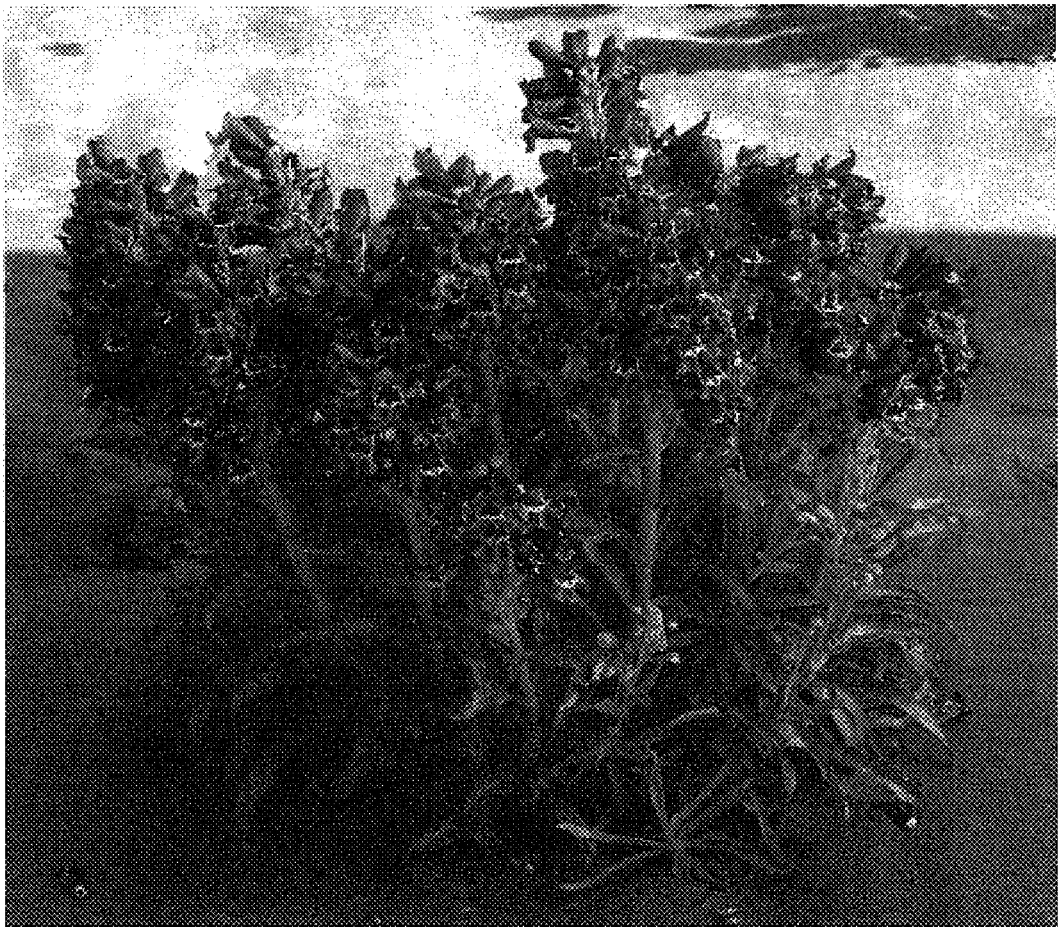

* * * * *